US00PP09902P

United States Patent [19]

Ackerman et al.

[11] Patent Number: Plant 9,902

[45] Date of Patent: May 27, 1997

[54] STRAWBERRY PLANT NAMED PS-776

[75] Inventors: Stephen M. Ackerman, Salinas; Steven D. Nelson; Michael D. Nelson, both of Watsonville; Peter Salm, Capitola; Daniel T. Schmida, Watsonville, all of Calif.

[73] Assignees: Plant Sciences, Inc.; Berry Red, Inc., both of Watonsville, Calif.

[21] Appl. No.: 584,221

[22] Filed: Jan. 11, 1996

[51] Int. Cl.[6] ..... A01H 5/00

[52] U.S. Cl. ..... Plt./49

[58] Field of Search ..... Plt./48, 49

*Primary Examiner*—James R. Feyrer

*Attorney, Agent, or Firm*—Foley & Lardner

[57] ABSTRACT

This invention relates to a new and distinct winter planted short-day-type variety of strawberry known as 'PS-776'. This new variety is primarily adapted to the growing conditions of the central coast of California. The new variety is particularly characterized by its small round leaves with many shallow serrations, long inflorescences which are easily visible above the canopy of the plant much of the season, very uniformly smooth shaped berries and its ability to remain in fruit production from mid to late April through November. The fruit is very attractive with acceptable flavor and juiciness as well as excellent firmness and holding quality.

3 Drawing Sheets

SUMMARY OF THE INVENTION

The present invention relates to a new and distinct short-day-type strawberry variety designated as 'PS-776'. This new variety is a result of a cross of the variety claimed in U.S. Pat. No. P.P. 8,205, now designated 'PS-118', and the variety claimed in U.S. Pat. No. P.P. 8,346, now designated 'PS-308'. The variety is botanically known as *Fragaria× ananassa* Duch.

This new variety of strawberry resulted from a breeding program jointly sponsored by Plant Sciences, Inc. and Berry R & D, Inc., both of Watsonville, Calif., with the objective of developing new and distinct strawberry varieties. The seedling resulting from the aforementioned cross was asexually propagated by stolons in a nursery located in Lassen County, Calif., and was subsequently selected from a controlled breeding plot in Watsonville, Calif. in 1991. After its selection, the new variety was further asexually propagated in Lassen County, Calif. by stolons and extensively tested over the next several years in fruiting fields near Watsonville, Calif. This propagation and reproduction has demonstrated that the combination of traits disclosed herein as characterizing the new variety are fixed and remain true-to-type through successive generations of asexual reproduction.

BRIEF DESCRIPTION OF THE FIGURES

The accompanying color photographs show typical specimens of the new variety at various stages of development as nearly true as it is possible to make in color reproductions.

DESCRIPTION OF THE NEW VARIETY

Figure 1:
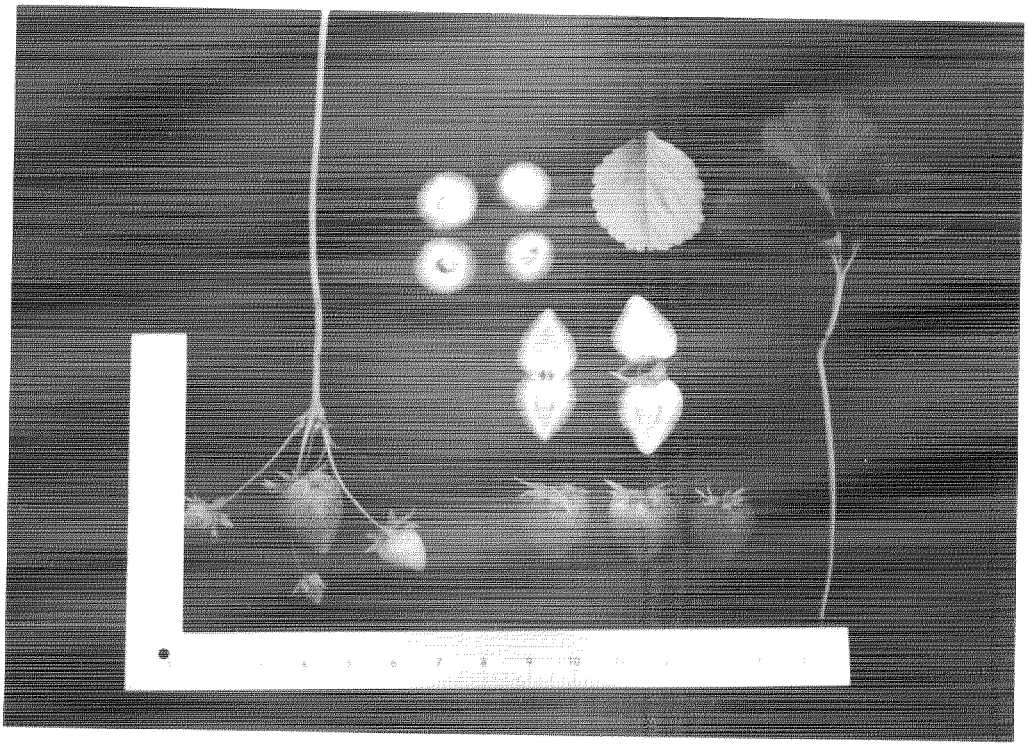
FIG. 1 shows typical plant parts of the new variety including leaves (both the lower surface of a mature terminal leaflet, and the upper surface of a mature trifoliate leaf). Cross-sectional and longitudinal views of mature fruit illustrate typical light flesh and conspicuous core and core cavity. Also shown is an inflorescence with the primary berry being mature and harvestable demonstrating typical fruit distribution, shape and size.
Figure 2:
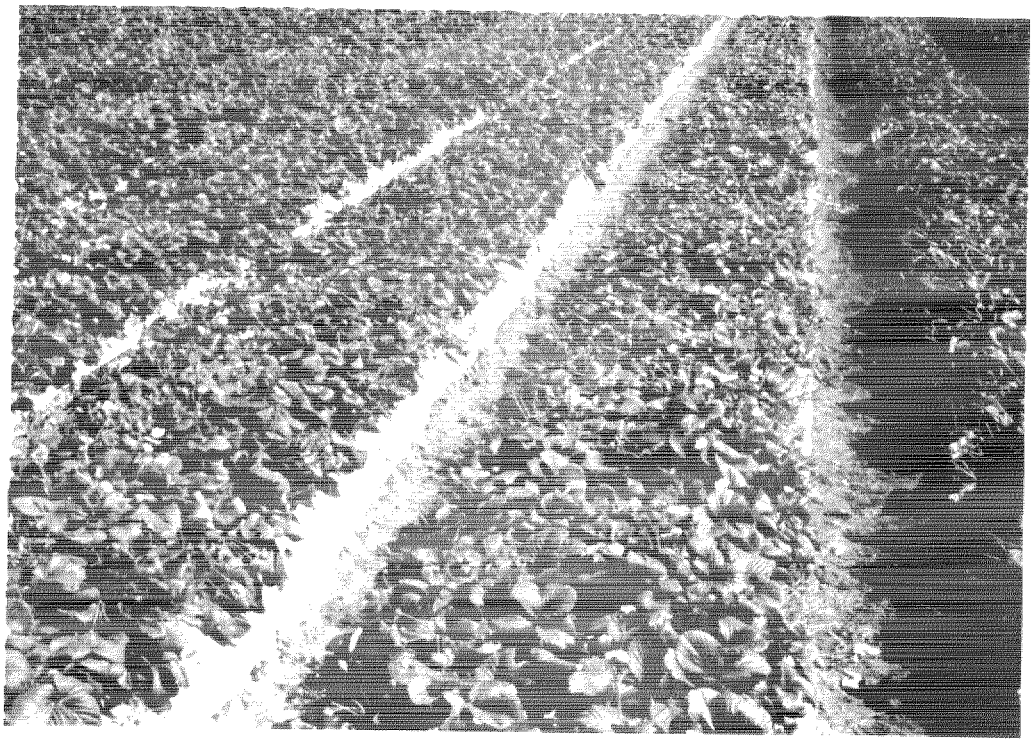
FIG. 2 shows typical plant growth, flowering and fruiting characteristics in late July 1995. The photograph illustrates the plant vigor, long inflorescences, and upright growth habit.
Figure 3:
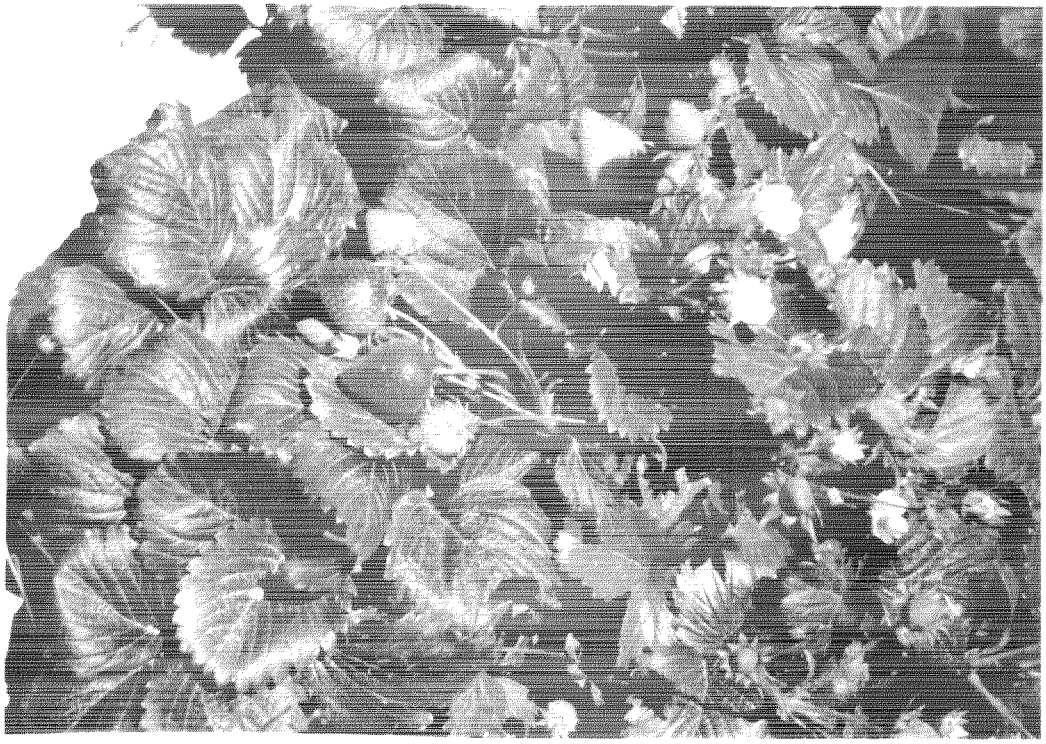
FIG. 3 shows a close-up of typical plant growth, flowering and fruiting characteristics in late July 1995.
Figure 4:
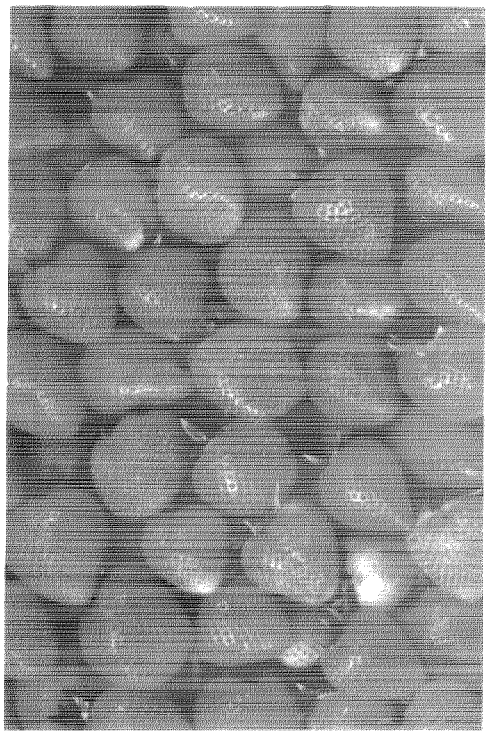
FIG. 4 shows a close-up view of fruit harvested in mid July 1995 and packed in a standard twelve-dry-pint-crate.
Figure 4:
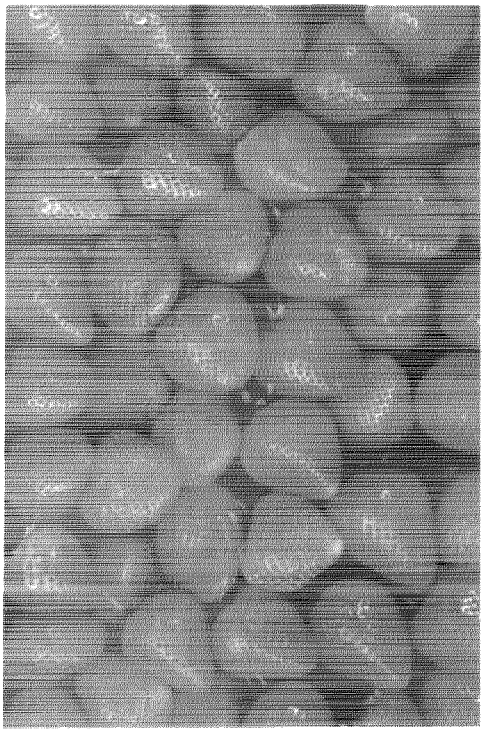

'PS-776' is primarily adapted to the climate and growing conditions of the central coast of California. This region provides the necessary winter temperatures required for it to produce a strong vigorous plant and to remain in fruit production from April through November. The nearby Pacific ocean provides the needed humidity and cool temperatures to maintain fruit quality during the summer production months.

'PS-776' is a moderately vigorous plant. When provided with optimum chilling in the nursery propagation fields prior to being dug, and artificial cold storage prior to being planted, the plant of the new variety tends to be smaller and less vigorous than both 'PS-118' and 'Selva' (U.S. Pat. No. P.P. 5,266). 'PS-776' generally produces fewer runners per plant in the fruiting fields than both 'PS-118' and 'Selva'. The foliage of the new variety is slightly darker in color than 'Selva' and slightly lighter than 'PS-118'. 'PS-776' leaves are smaller than both 'PS-118' and 'Selva' and more rounded in shape than 'Selva'. 'PS-776' has more serraions per leaf and shallower serrations than both 'PS-118' and 'Selva'. 'PS-776' petioles are similar in length, but smaller in diameter, than both 'PS-118' and 'Selva'. Table 5 summarizes foliage characteristics of 'PS-776', 'PS-118' and 'Selva'.

'PS-776' is capable of long season fruit production with fruit of acceptable size and excellent quality during the entire season when provided with optimum chilling in the nursery propagation fields and artificial cold storage prior to being planted. Initial studies indicate that 'PS-776' has a lower vernalization (chilling) requirement than 'Selva' for optimum fruit production and plant vigor. Fruit production begins as early as mid April in Salinas, Calif., and may continue into November if rains and cold temperatures do not prevent the harvest. April production is later and lighter than 'Selva' and similar to 'PS-118'. 'PS-776' season average fruit size is smaller than both 'PS-118' and 'Selva' with total yields comparable to both (Table 1).

The fruit of 'PS-776' is smoother with fewer longitudinal creases and better overall appearance, gloss and skin firmness than 'Selva'. Table 3 summarizes fruit quality performance ratings. The primary berries of 'PS-776' tend to produce seedy tips at the apex of the fruit primarily during the early spring and under adverse weather conditions. In comparison, 'PS-118' tends to produce seedy tipped fruit during much of the season. The seeds of 'PS-776' typically do not protrude, or only slightly protrude, from the surface of the fruit. In contrast 'PS-118' tends to have seeds that protrude more consistently from the fruit surface. The fruit color of 'PS-776' is noticeably darker than 'Selva' but similar to 'PS-118'. 'PS-776' fruit has a lighter internal flesh color than either 'PS-118' or 'Selva'. The fruit of 'PS-776' is very smooth and symmetrically conic. It is more conical in shape (less rounded) than the fruit produced by 'PS-118'. The fruit is also smoother and more uniformly conic, with fewer longitudinal creases and irregular shapes, than 'Selva'.

Flavor panels have rated 'PS-776' as having better flavor than 'Selva' (Table 4). The fruit of 'PS-776' is more susceptible to skin cracking from rain than the fruit produced by either 'PS-118' or 'Selva'. The total inflorescence length of 'PS-776' is considerably longer than 'PS-118', especially during the summer months. The average primary peduncle is longer and thinner than both 'PS-118' and 'Selva'. The primary pedicel is also shorter and thinner than both. Flowers and ripening fruit are noticeably more visible above the canopy of the plant during much of the season as compared to 'PS-118' and 'Selva'. Table 6 summarizes inflorescence characteristics of 'PS-776', 'PS-118' and 'Selva'.

SPECIFIC DESCRIPTION OF THE NEW VARIETY

The following is a detailed description of 'PS-776', including the variety's morphological, electrophoretic, pest and disease reaction characteristics. This detailed description is based on observations taken during May through July of 1995 in Salinas, Calif. In those instances where a characteristics was rated at different times the date of the evaluation is listed. These measurements and ratings were made from plants dug from a high-elevation nursery located in Lassen County, Calif. in October 1994 and planted in Salinas, Calif. in November 1994. The phenotypic characteristics of the new variety may vary slightly, depending upon variations in environmental factors, including weather (temperature, humidity and light intensity), day length, soil type, location, and time of year, without a change in the genotpe of the plant. 'PS-776' has not been observed under all possible environmental conditions. Color terminology follows the Munsell Book of Colors, Munsell Color, Baltimore, Md. (1976).

FRUIT CHARACTERISTICS

'PS-776' fruit, fruit production and runner production (fruiting field) characteristics are compared to those of 'PS-118' and 'Selva' in Table 1.

TABLE 1

1994 market fruit yield, fruit size and runner production characteristics from plants harvested from April through November 1994 of 'PS-776' from a high elevation nursery (McArthur, California) compared with standard cultivars dug October 20, 1993 and planted November 9, 1993 in Salinas, California.

| CULTIVAR | APRIL YIELD GM/PL | TOTAL YIELD GM/PL | AVERAGE FRUIT SIZE G/FR | AVERAGE RUNNERS/ PL |
|---|---|---|---|---|
| 'PS-776' | 33 | 1499 | 20.4 | 0.20 |
| 'PS-118' | 43 | 1351 | 21.7 | 0.12 |
| 'SELVA' | 90 | 1414 | 22.8 | 0.20 |

TABLE 2

Comparison of primary fruit characteristics of 'PS-776', 'PS-118' and 'Selva' from Salinas, California, July 27, 1995.*

| CHARACTER | 'PS-776' | 'PS-118' | 'SELVA' |
|---|---|---|---|
| Munsell Color | 7.5R 3/8 to 7.5R 3/10 | 7.5R 3/10 to 7.5R 3/8** | 7R 4/11** |
| Fruit Length mean (cm) | 3.5 | 3.8 | 4.4 |
| Fruit Width mean (cm)*** | 3.3 | 4.0 | 4.2 |
| Calyx Diameter mean (cm) | 3.7 | 5.4 | 4.1 |
| Sepals/Berry mean | 14.1 | 15.0 | 15.8 |

*'PS-118' and 'Selva' evaluated July 17, 1995.
**'PS-118' and 'Selva' fruit color according to Nelson et al, U.S. Plant Pat. No. 8,205.
***Width is measured across the widest part of the berry, typically across the shoulders.

TABLE 3

Comparison of 1994 fruit quality characteristics of 'PS-776', 'PS-118' and 'Selva', from Salinas, California.*

| CHARACTER | 'PS-776' | 'PS-118' | 'SELVA' |
|---|---|---|---|
| Skin Firmness | 8.0 | 8.3 | 7.6 |
| Fruit Appearance | 8.3 | 7.7 | 6.8 |
| Fruit Gloss | 8.0 | 8.2 | 6.6 |

*Results are from replicated holding tests performed from April through October 1994 in Salinas, California. Ratings are based on a scale from 1–10; the higher the rating, the stronger the skin and the more attractive and glossy the berry.

TABLE 4

Comparison of 1995 flavor test summary of 'PS-776', 'PS-118' and 'Selva'.*

| CHARACTER | 'PS-776' | 'PS-118' | 'SELVA' |
|---|---|---|---|
| Rating | 2.6 | 3.5 | 2.4 |

*Results are an average of 3–4 flavor tests from fruit harvested from Salinas, California after being held for 2–3 days in cold storage. Ratings are based on scores of 1–5, 5 being the best.

The fruit of 'PS-776' is medium-small in size and characteristically conic in shape. Primary berries are typically longer than wide with longitudinal creases and irregular shapes occurring infrequently. The secondary and tertiary berries are also typically longer than wide and symmetrically conic in shape. The fruit surface is medium to deep red in color with a very light colored flesh to white at the core. Table 2 summarizes fruit comparison characteristics.

The fruit surface is typically smooth with the seeds generally held flush to the surface with some seeds protruding slightly from the fruit surface. The seeds are yellow and only darken slightly with prolonged exposure to direct sunlight. The seeds are spaced evenly over the surface of the berry with seedy tipped fruit rare except for early spring primary berries which may have seedy tips. The fruit becomes more uniformly shaped producing seedy tips rarely during the summer and fall months. The skin of the fruit is considered firm, with good gloss and acceptable flavor. Tables 3 and 4 summarize fruit quality and flavor characteristics, respectively.

The calyx of the primary berry is relatively small in diameter with some overlapping sepals. The calyx attaches slightly below the base of the fruit with necked fruit very uncommon. The sepals are elliptical to ovate in shape with acute apexes and very few serrations. Fruit skin is considered very susceptible to cracking due to rain. Pollination may be affected by rain resulting in seedy tipped fruit and small malformed berries.

PLANT CHARACTERISTICS

The plant of 'PS-776' is medium in size with multiple crowns producing very few runners when given the proper chilling levels prior to being dug, and artificially, prior to being planted. Excessive chilling will result in an over-vigorous plant with a reduction in total fruit yield and increased runner production. Although the plant may become over vigorous if provided with excessive field chilling and/or artificial cold storage prior to being planted, it generally does not become too large unless chilling and/or storage levels greatly exceed acceptable limits. The plants grow slowly during the winter and spring months after planting, but by early summer have reached good vigor. The foliage grows upright on relatively long thin petioles. The plant canopy remains relatively open if exposed to the proper chilling and cold storage levels, but may become slightly more dense if over-chilled and/or over-stored. The plant canopy has a relatively medium-colored appearance, yet may appear lighter than normal due to the greater inflorescence exposure above the plant.

FOLIAGE CHARACTERISTICS

'PS-776' foliage characteristics are compared to those of 'PS-118' and 'Selva' in Table 5.

TABLE 5

Comparison of leaf characteristics of 'PS-776', 'PS-118' and 'Selva' from Salinas, California, May 19, 1995.

| CHARACTER | 'PS-776' | 'PS-118' | 'SELVA' |
|---|---|---|---|
| Munsell Leaf Color (upper surface) | 7.5GY ¾ to 7.5GY ⅜ | 7.5GY ¾* | 7.5GY ¼* |
| Terminal Leaflet length mean (cm) | 7.7 | 8.4 | 9.8 |
| Terminal Leaflet width mean (cm) | 7.4 | 7.7 | 8.3 |
| Terminal Leaflet ratio (L/W) | 1.04 | 1.09 | 1.19 |
| Petiole Length mean (cm) | 19.9 | 20.1 | 19.8 |
| Petiole Width mean (mm) | 4.4 | 4.7 | 5.2 |
| Petiolule Length | 9.7 | 10.0 | 10.8 |

TABLE 5-continued

Comparison of leaf characteristics of 'PS-776', 'PS-118' and 'Selva' from Salinas, California, May 19, 1995.

| CHARACTER | 'PS-776' | 'PS-118' | 'SELVA' |
|---|---|---|---|
| mean (mm) | | | |
| Serrations/Leaf | 25.7 | 20.7 | 24.9 |
| Serration Depth mean (mm) | 4.3 | 5.8 | 5.2 |

*'PS-118' and 'Selva' leaf color according to Nelson et al., U.S. Plant Pat. No. 8,205.

The foliage of 'PS-776' is relatively small in size, non-glossy, medium in color and lightly rugose. The terminal leaflet is nearly as wide as long as described by the length/width ratio. Table 5 summarizes foliage comparison characteristics. Leaflets have many relatively small and shallow serrations at the margins with moderately acute apexes. These serrations typically occur singly with many leaves having small double serrations the point where the serrations join. Petioles are considered long and thin in diameter with bract leaflets commonly occuring singly or in pairs. Petioles are medium in length. Pubescence on the petioles grows irregularly perpendicular to the petiole and irregularly parallel to the upper and lower leaf surface.

FLOWERS AND INFLORESCENCES

'PS-776' inflorescence characteristics are compared to those of 'PS-118' and 'Selva' in Table 6.

TABLE 6

Comparison of inflorescence characteristics of 'PS-776', 'PS-118' and 'Selva' from Salinas, California, July 27, 1995.*

| CHARACTER | 'PS-776' | 'PS-118' | 'SELVA' |
|---|---|---|---|
| Inflorescence Length mean (cm) | 36.3 | 30.8 | 36.0 |
| Primary Peduncle Length mean (cm) | 26.2 | 19.0 | 20.0 |
| Primary Peduncle Width mean (mm) | 3.4 | 4.2 | 4.2 |
| Primary Pedicel Length mean (cm) | 4.9 | 6.3 | 9.0 |
| Primary Pedicel Width mean (mm) | 1.8 | 2.3 | 2.5 |

*'PS-118' and 'Selva' evaluated July 17, 1995.

The inflorescence of 'PS-776' is long, extending the flowers and fruit beyond the foliage during much of the season. The inflorescence remains upright, visible above the plant canopy much of the year, until the weight of the ripening fruit causes then to fall to the sides of the bed. The primary peduncle is considered long and thin, especially at the time of the evaluation. The pedicel holding the primary berry is considered short and thin and may originate singly from the apex of the primary peduncle or from one of the secondary peduncles. Secondary and tertiary berries are borne on pedicels arising from secondary peduncle apexes. Anthocyanin coloration (color near 5R 4/8) is present on exposed surfaces of primary pedicels and secondary and tertiary pedicels and peduncles. Table 6 summarizes inflorescence comparison characteristics.

Flowers are medium in size and readily seen above the canopy of the plant during much of the season. Anthers produce ample pollen for good pollination except during the early season and rainy periods when seedy tipped fruit may occur. Flowers produce an average of 6 to 9 small obovate shaped petals per flower. Typically a bract leaf is borne on a short petiole which originates at the primary peduncle apex alongside the base of one of the secondary peduncles. Bract leaves may also occur at the apex of secondary peduncles. Pubescence occurs on all peduncles and pedicels, growing irregularly perpendicular to both these surfaces.

ISOZYMES IN LEAF EXTRACT

'PS-776' isozyme banding characteristics are compared to those of 'PS-118' and 'Selva' in Table 7.

TABLE 7

'PS-776' Isozyme banding patters compared to 'PS-118' and 'Selva'.

| CULTIVAR | PGI | PGM |
|---|---|---|
| 'PS-776' | A2 | C4 |
| 'PS-118' | A7 | C4 |
| 'Selva' | A2 | C2 |

Studies of protein polymorphism in strawberry by the starch gel electrophoresis method were conducted at Plant Sciences, Inc. to characterize this newly developed variety and distinguish it from similar appearing varieties.

Isozymes were extracted from young leaves and characterized, using starch gel electrophoresis techniques. The following isozmes were characterized: phosphoglucoisomerase (PGI:EC 5.3.1.9) and phosphoglucomutase (PGM:EC 2.7.5.1).

The testing used both field and greenhouse grown plant material, all grown in Watsonville, Calif. Newly mature leaves (0.5 g fresh weight) from the growing crowns were used. Samples collected in the morning, held at 4° C. and analyzed within six hours.

The tissue preparation, extraction and staining methods utilized are as reported in S. Arulsekar and D. E. Parfitt, "Isozyme Analysis Procedures for Stone Fruits, Almond, Grape, Walnut, Pistachio, and Fig", HortScience 21(4): 928–933.

Following electrophoresis, the gel was sliced and stained for each enzyme system. Banding patterns were interpreted as they developed and gel slices were fixed in 50% glycerol.

Figure 5:
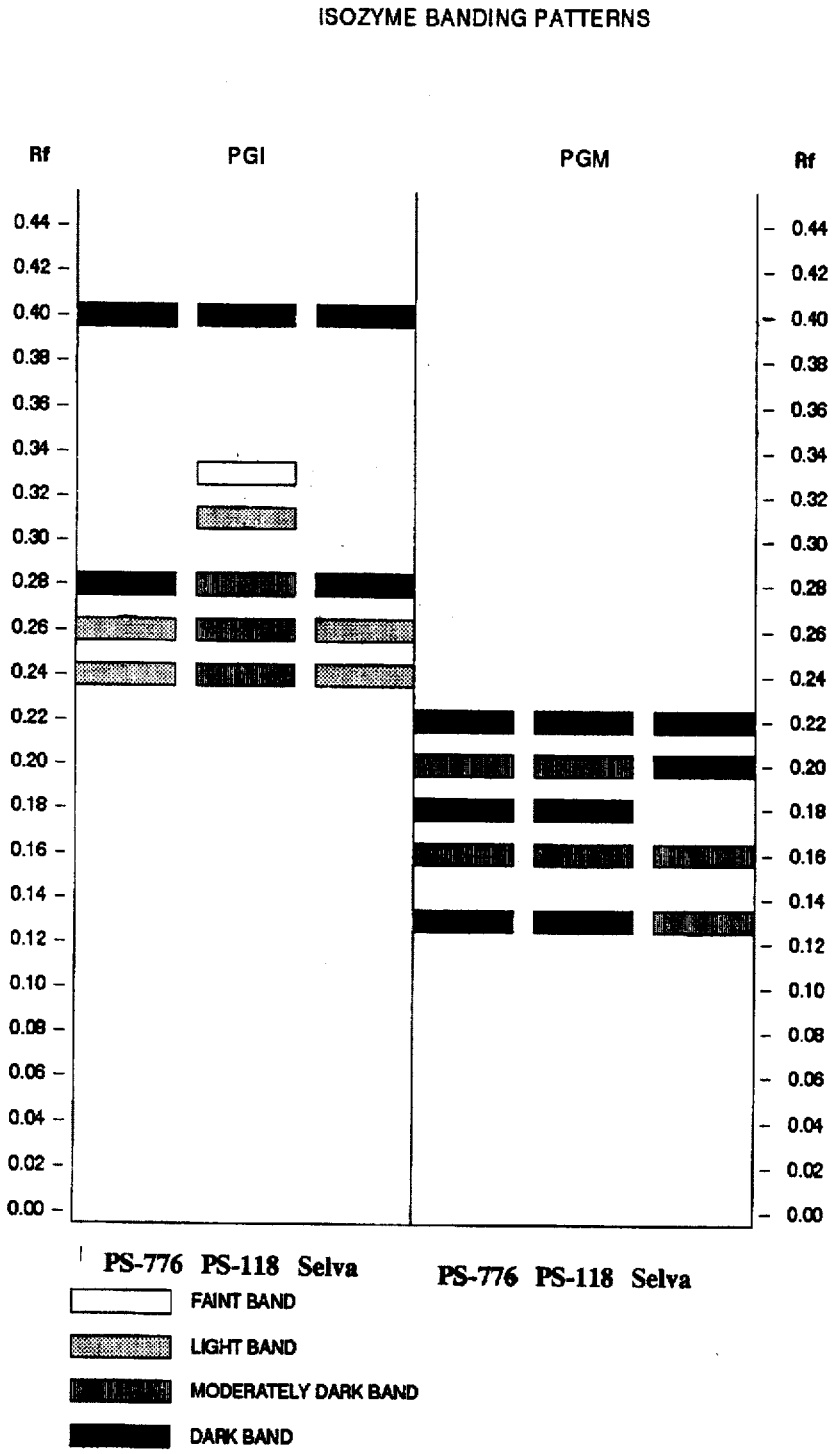
FIG. 5 discloses the isozyme banding patterns for 'PS-776', compared with those of 'PS-118' and 'Selva'.

The isozyme banding patterns of 'PS-776', compared to 'Selva' and 'PS-118', are given in FIG. 5. The pattern and band densities are distinctly different between 'PS-776' (C4) and 'Selva' (C2) for the PGM enzyme system. The pattern and band densities are distinctly different between 'PS-776' (A2) and 'PS-118' (A7) for the PGI enzyme system. The combination of isozyme patterns shown, derived from the specific techniques described, identify 'PS-776' with certainty as a unique strawberry variety.

A series of molecular markers have been assigned to this new variety for unique identification.

PEST REACTIONS

The new variety may not be resistant to any of the known insects, diseases or viruses common in California. It is known to be susceptible to the two-spotted spider mite, aphid and flower thrip. It is also known to be susceptible to grey fruit mold, angular leafspot and powdery mildew. The susceptibility of the new variety to any of the virus complexes of California has not been determined.

We claim:

1. A new and distinct variety of strawberry plant designated 'PS-776', as herein described and illustrated.

* * * * *

UNITED STATES PATENT AND TRADEMARK OFFICE

CERTIFICATE OF CORRECTION

PATENT NO. : PP 9,902

DATED : May 27, 1997

INVENTOR(S) : Stephen M. ACKERMAN, et al.

It is certified that error appears in the above-identified patent and that said Letters Patent is hereby corrected as shown below:

Item [73], Assignee "Berry Red, Inc." should read --Berry R & D, Inc.--.

Signed and Sealed this

Eighth Day of August, 2000

*Attest:*

*Attesting Officer*

Q. TODD DICKINSON

*Director of Patents and Trademarks*